(12) United States Patent
Spivey et al.

(10) Patent No.: US 9,261,306 B2
(45) Date of Patent: Feb. 16, 2016

(54) ATOMIZING FURNACE

(71) Applicants: Christopher Spivey, Lodi, CA (US);
Ching-Tung Yong, Singapore (SG);
Gerhard Schlemmer, Weimar (DE);
Rudolf Weck, Sinn (DE); Ralf Gaertner, Lahnau (DE)

(72) Inventors: Christopher Spivey, Lodi, CA (US);
Ching-Tung Yong, Singapore (SG);
Gerhard Schlemmer, Weimar (DE);
Rudolf Weck, Sinn (DE); Ralf Gaertner, Lahnau (DE)

(73) Assignee: SCHUNK KOHLENSTOFFTECHNIK GMBH, Heuchelheim (DE)

( * ) Notice: Subject to any disclaimer, the term of this patent is extended or adjusted under 35 U.S.C. 154(b) by 316 days.

(21) Appl. No.: 13/666,035

(22) Filed: Nov. 1, 2012

(65) Prior Publication Data

US 2014/0118734 A1    May 1, 2014

(51) Int. Cl.
*G01N 21/74* (2006.01)
*F27D 5/00* (2006.01)
*G01N 21/31* (2006.01)

(52) U.S. Cl.
CPC ...... *F27D 5/0068* (2013.01); *F27D 2005/0081* (2013.01); *G01N 21/3103* (2013.01); *G01N 21/74* (2013.01)

(58) Field of Classification Search
None
See application file for complete search history.

(56) References Cited

U.S. PATENT DOCUMENTS

| 4,971,438 | A |   | 11/1990 | Hutsch et al. |
| 5,083,864 | A |   | 1/1992 | Huetsch et al. |
| 5,949,538 | A | * | 9/1999 | Eichardt ............... G01N 21/74 356/312 |

FOREIGN PATENT DOCUMENTS

| CN | 1540316 A | 10/2004 |
| DE | 4240934 A1 | 6/1994 |
| DE | 19932874 A1 | 2/2001 |
| EP | 0442009 A1 | 8/1991 |

OTHER PUBLICATIONS

European Patent Office, Search Report, Application No. 13187955, Feb. 7, 2014, 6 pages.
State Intellectual Property Office of People's Republic of China, First Office Action and Search Report, Application No. 201310526099.4, Sep. 14, 2015 [English Language Translation Only].

* cited by examiner

*Primary Examiner* — Michael A Lyons
*Assistant Examiner* — Amanda Merlino
(74) *Attorney, Agent, or Firm* — Quarles & Brady LLP

(57) ABSTRACT

An atomizing furnace, in particular for atomic absorption spectroscopy, includes a tube furnace apparatus and a sample carrier. The sample carrier is disposed within the tube furnace apparatus, and includes at least three supporting protrusions by which the sample carrier is punctually supported on an interior wall of the tube furnace apparatus. The supporting protrusions are disposed in a common plane running through a longitudinal axis of the sample material, wherein at least two supporting protrusions are formed on respectively opposite ends of the sample carrier.

9 Claims, 2 Drawing Sheets

ATOMIZING FURNACE

CROSS REFERENCES TO RELATED APPLICATIONS

Not Applicable.

STATEMENT REGARDING FEDERALLY SPONSORED RESEARCH

Not Applicable.

FIELD OF THE INVENTION

The invention relates to an atomizing furnace, in particular for atomic absorption spectroscopy, comprising a tube furnace apparatus and a sample carrier, wherein the sample carrier serves the purpose of taking up an analyte, wherein the sample carrier is disposed within the tube furnace apparatus, wherein the sample carrier comprises at least three supporting protrusions by which the sample carrier is punctually supported on an interior wall of the tube furnace apparatus.

DESCRIPTION OF THE BACKGROUND ART

Atomizing furnaces typically comprise a graphite tube which essentially forms the tube furnace apparatus. The graphite tube comprises graphite contacts which are disposed on the graphite tube such that high currents can run via the graphite tube in longitudinal or transverse direction in order to heat the graphite tube. Within the graphite tube a sample carrier is disposed, which can also be formed from graphite. On the sample carrier an analyte or sample can be placed, which is heated to a temperature high enough for the sample to be atomized. In order to identify the proportions of the elements of the sample, a measuring light beam is sent through a longitudinal drill hole in the tube furnace part. It is substantial for the measuring results that no electric heating current be running through the sample carrier. Further it must be avoided that the sample carrier is directly heated by heat conduction via a contact with the graphite tube. Additionally, a stable fixation of the sample carrier within the tube furnace apparatus is necessary in order to avoid a displacement of the sample carrier in relation to the tube furnace apparatus or a tilting of the sample carrier.

From DE 199 32 874 C2 an atomizing furnace is known in which a sample carrier is disposed within a tube furnace apparatus and punctually supported on a wall of the tube furnace apparatus by three or four supporting protrusions. The supporting protrusions therein are formed in a middle of the sample carrier on its circumference in relation to a length of the sample carrier. The supporting protrusions are further disposed in three planes that run transversally to a longitudinal axis of the sample carrier.

In the afore described sample carrier a relatively low heat conduction via the supporting protrusions is provided, thus enabling a particularly good indirect heating of the analyte, as opposed to comparably large supports that could for example be formed as a ring on the circumference of the sample carrier or in the form of a beam. Consequently, any enlargement of the supporting protrusions or of their contact area to the tube furnace apparatus leads to an improved direct heat conduction, which here is undesirable, in particular for an analysis. Further, the alignment of the supporting protrusions of the known sample carrier is disadvantageous since in the case of a transverse heating, meaning a feeding of power on the tube furnace apparatus transversally to the longitudinal axis of the tube furnace apparatus, a particularly good current flow through the sample carrier is given. This can be largely eliminated for the position of the supporting protrusions in the middle of the sample carrier for a longitudinal heating, meaning feeding power into the respective ends of the tube furnace apparatus, since then the supporting protrusions have the same electric potential. Yet it is desirable that the sample carrier and the atomizing furnace be suitable for both transverse and longitudinal heating. Another disadvantage that arises from the alignment of the supporting protrusions in the sample carrier of DE 193 28 74 C2 is the static support of the sample carrier of the tube furnace apparatus. Since the supporting protrusions are formed in the middle of the sample carrier, the sample carrier can easily tilt in relation to the tube furnace apparatus. This particularly pertains to a correct positional assembly and fixation of the sample carrier within the tube furnace apparatus.

SUMMARY OF THE INVENTION

The present invention has the task of proposing an atomizing furnace in which good indirect heat conduction is possible and, moreover, which resolves the disadvantages in supporting the sample carrier known from the state of the art.

In one embodiment of the invention, this task is solved by an atomizing furnace with the attributes disclosed herein. The atomizing furnace according to the invention, in particular for atomic absorption spectroscopy, comprises a tube furnace apparatus and a sample carrier, wherein the sample carrier serves the purpose of taking up an analyte, wherein the sample carrier is disposed within the tube furnace apparatus, wherein the sample carrier comprises at least three supporting protrusions by which the sample carrier is punctually supported on an interior wall of the tube furnace apparatus, wherein the supporting protrusions are disposed in a common plane running through a longitudinal axis of the sample carrier, wherein at least two supporting protrusions are formed on two respectively opposite ends of the sample carrier.

It becomes possible to position the sample carrier with at least one three-point support on the interior wall of the tube furnace in particular due to the fact that at least two supporting protrusions are disposed on the respectively opposite ends of the sample carrier and that at least one additional supporting protrusion is formed on the sample carrier. A three-point support is particularly effective in preventing a tilting of the sample carrier in relation to the tube furnace apparatus. Since the supporting protrusions are disposed in a common plane running through a longitudinal axis of the sample carrier, a position of the supporting protrusions on the sample carrier can be chosen such that a power current through the sample carrier can be obstructed and therefore minimized due to the relative distance between the supporting protrusions. At the same time it is possible, due to the punctual support of the sample carrier on the tube furnace apparatus, to minimize direct heat conduction onto the sample carrier.

In one embodiment of the invention the sample carrier can comprise three supporting protrusions, wherein one supporting protrusion can be formed on mid-length between the two ends of the sample carrier. Then the distances between the supporting protrusions are maximized in relation to each other, so that this alignment of the supporting protrusions is particularly suitable for both transversal and longitudinal heating of the atomizing furnace. In consequence, currents running in transverse as well as longitudinal direction through the sample carrier have to travel relatively far and therefore overcome a higher resistance through the sample carrier. The resulting increased resistance can minimize the undesirable current flow.

In a second embodiment the sample carrier can comprise four supporting protrusions, wherein respectively two supporting protrusions are formed on opposite sides of the sample carrier. Since less than five supporting protrusions can be formed on the sample carrier, production of the sample carrier becomes particularly cost-efficient because no supporting protrusions that are essential for a sufficient static positioning of the sample carrier within the tube furnace apparatus have to be formed. The supporting protrusions, which then lie opposite relative to the longitudinal axis of the sample carrier, respectively have the same electric potential which makes the sample carrier particularly suitable for longitudinal heating.

Preferably, the supporting protrusions can protrude radially from the sample carrier. Then the supporting protrusions can be formed particularly easy as one piece. Also, the sample carrier can then be formed as a closed or open tube profile which can be easily adapted to a tube furnace apparatus or be positioned in one.

The supporting protrusions can further be formed in a biggest possible distance in relation to a cross section of the sample carrier Preferably, the supporting protrusions can be formed on the sample carrier in such a way that a heating current must pass the sample carrier on a relatively long way. A cross section of the sample carrier can further be formed as an arc. The arc carrier is then open on an upper side so that an analyte can be easily placed into the sample carrier. Preferably, for a simpler manufacture, the arc can be a circular arc.

Advantageously the common plane can run through a central point of the arc. Consequently the supporting protrusions can be disposed in the area of the ends of the arc. The sample carrier is even more easily produced if the arc is formed as a half circle. Also, the sample carrier can be formed as a vat, meaning the opposite ends of the sample carrier can be formed in such a way that a vat-like receiving space for an analyte is formed. This way it can be made sure that the analyte cannot simply fall out of the sample carrier.

The supporting protrusions can have a rectangular geometry and have a radius in a transition area to a base body of the sample carrier. Such a form of the supporting protrusions can be easily achieved by machine processing of a blank of the sample carrier, which simplifies manufacture of the sample carrier. Further, crack formation between the base body and the supporting protrusion is avoided by forming radii in the transition area.

The sample carrier can be fixed within the tube furnace apparatus by pyrolytic coating. During the manufacture of the atomizing furnace the sample carrier can be positioned in the tube furnace apparatus, wherein an afterwards application of the pyrolytic coating on the surface of the sample carrier in the tube furnace apparatus can firmly connect both building parts.

In order to be able to easily provide the sample carrier disposed within the tube furnace apparatus with an analyte, the tube furnace apparatus can comprise an opening for inserting analytes. The opening for inserting analytes can for example be formed as a transverse drill hole in the tube furnace apparatus and enable a particularly easy positioning of the analyte on the sample carrier.

BRIEF SUMMARY OF THE DRAWINGS

In the following a preferred embodiment of the invention is explained in more detail under reference of the enclosed drawings.

DETAILED DESCRIPTION OF THE PREFERRED EMBODIMENTS

Figure 1:
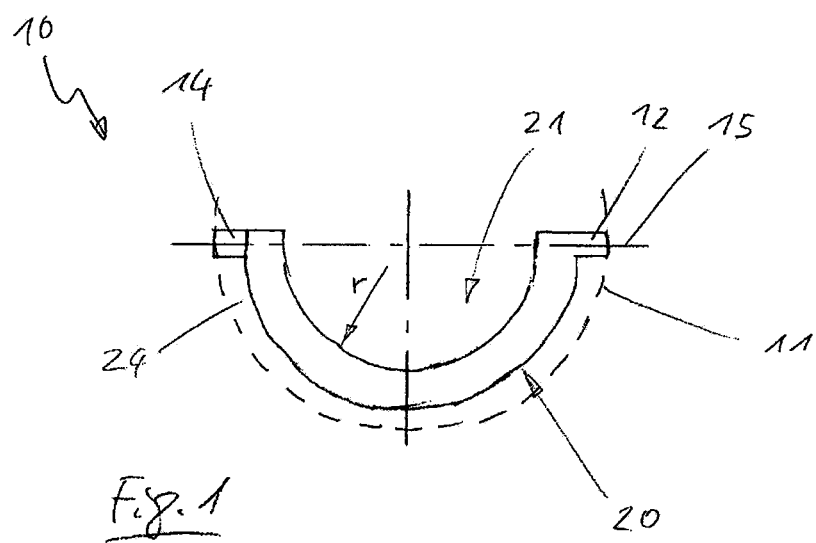
FIG. 1 shows a lateral view of a sample carrier in the direction of a longitudinal axis of the sample carrier.
Figure 2:
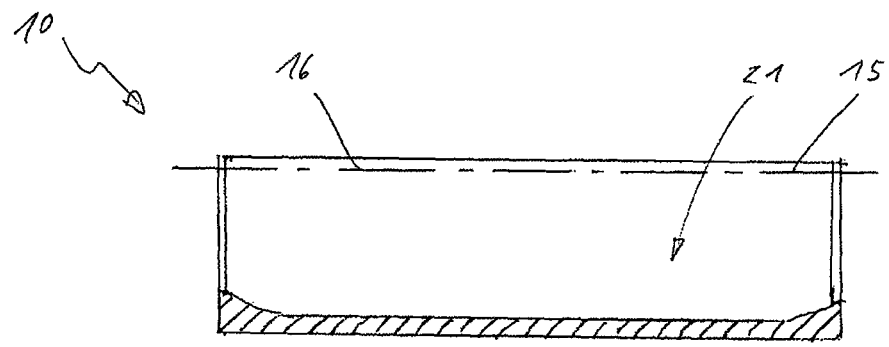
FIG. 2 shows a longitudinal sectional view of a sample carrier.
Figure 3:
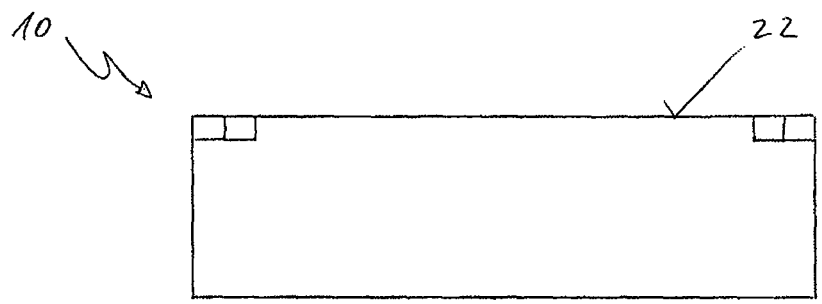
FIG. 3 shows a frontal view of the sample carrier.
Figure 4:
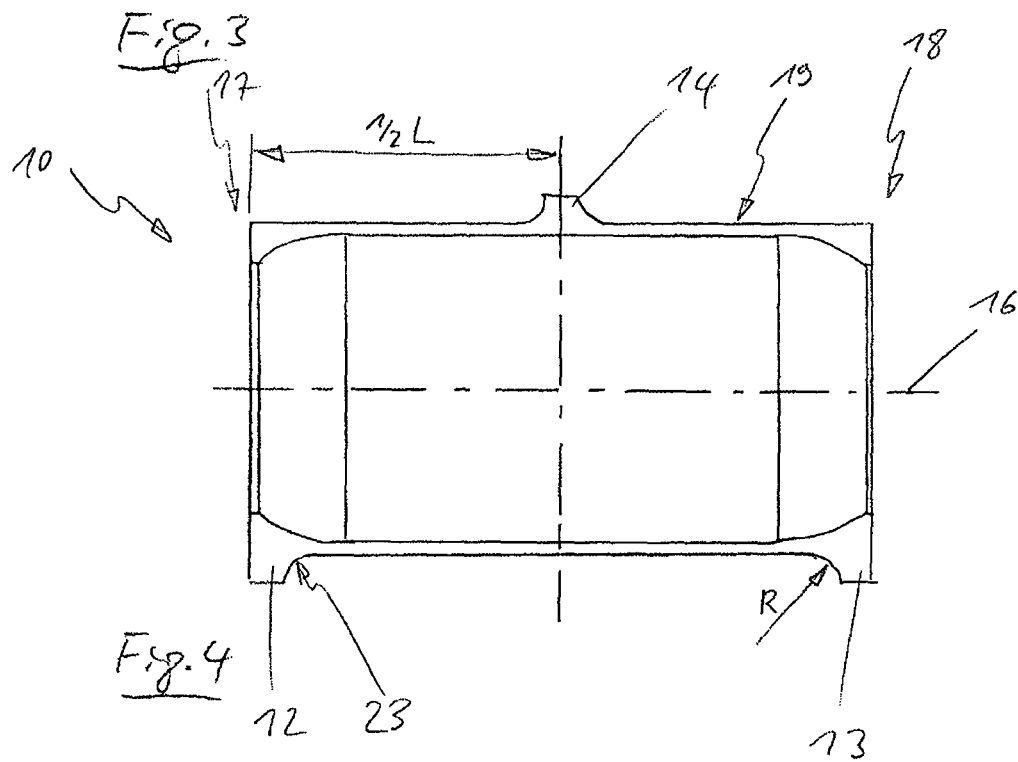
FIG. 4 shows a top view of the sample carrier.

A collective view of the FIGS. 1 to 4 shows an embodiment of a sample carrier 10 for an atomizing furnace not illustrated in further detail here. The sample carrier 10 can be inserted into a tube furnace apparatus not illustrated here either. An interior wall 11 of the tube furnace apparatus is suggestively illustrated in a dashed outline.

The sample carrier comprises three supporting protrusions 12, 13, and 14, wherein they are disposed in a common plane 15 and wherein the plane 15 runs through a longitudinal axis 16 of the sample carrier 10. The longitudinal axis 16 corresponds with a longitudinal axis of the tube furnace apparatus not illustrated in further detail. In particular, the supporting protrusions 12 and 13 are formed on the respectively opposite ends 17 and 18 of the sample carrier 10 on one side of the sample carrier. The supporting protrusion 14 is formed at mid-length (L) between the ends 17 and 18 of the sample carrier 10 on an opposing side of the sample carrier to separate the protrusions 12, 13, 14 from each other by the farthest distance possible within a cross section of the sample carrier.

A base body 19 of the sample carrier 10 is formed as an arc 20 in the form of a half circle in direction of the cross section. On the ends 17 and 18 an inner radius (r) of the arc 20 is formed, such that a vat-like receiving space 21 is formed for an analyte not illustrated here.

The supporting protrusions 12 and 13 are formed opposite of the supporting protrusion 14 in relation to the longitudinal axis 16 on the sample carrier 10. The sample carrier 10 can therefore be fixed to the interior wall 11 of the tube furnace apparatus at three points, wherein between the interior wall 11 of the tube furnace apparatus and the base body 19 of the sample carrier 10 an annular gap 24 is formed.

The supporting protrusions 12, 13, and 14 are further formed on an upper edge 22 of the sample carrier 10 and have a rectangular geometry. In the transition area 23 with the base body 19 of the sample carrier 10 a radius (R) is formed.

While there has been shown and described what are at present considered the preferred embodiments of the invention, it will be obvious to those skilled in the art that various changes and modifications can be made therein without departing from the scope of the invention defined by the appended claims.

The invention claimed is:

1. An atomizing furnace for atomic absorption spectroscopy, said furnace comprising:
   a tube furnace apparatus; and
   a sample carrier disposed within the tube furnace apparatus, wherein the sample carrier has a cross-section defining an arc formed as a half circle, and serves the purpose of taking up an analyte, the sample carrier consisting of three supporting protrusions punctually supporting the sample carrier on an interior wall of the tube furnace apparatus, the supporting protrusions being disposed in a common horizontal plane running through a longitudinal axis of the sample carrier, wherein two of the supporting protrusions are formed on respectively opposite ends of the sample carrier, and one of the supporting protrusions is formed at mid length between the ends of the sample carrier.

2. The atomizing furnace according to claim 1, in which the three supporting protrusions protrude radially from the sample carrier.

3. The atomizing furnace according to claim 1, in which the three supporting protrusions are separated by a largest possible distance in relation to a cross section of the sample carrier.

4. The atomizing furnace according to claim 1, in which a common plane runs through a central point of the arc.

5. The atomizing furnace according to claim 1, in which the sample carrier is a vat.

6. The atomizing furnace according to claim 1, in which the supporting protrusions have a rectangular geometry and have a radius (R) in a transitional area to a base body of the sample carrier.

7. The atomizing furnace according to claim 1, in which the tube furnace apparatus comprises an opening for inserting analytes.

8. The atomizing furnace according to claim 1, in which the interior wall of the tube furnace apparatus is a radially inwardly facing wall, and said supporting protrusions engage a radially inwardly facing surface of said radially inwardly facing wall to support said sample carrier in said tube furnace apparatus.

9. The atomizing furnace according to claim 1, in which the sample carrier is fixed within the tube furnace apparatus by a pyrolytic coating.

* * * * *